United States Patent [19]

Bernard et al.

[11] Patent Number: 5,637,753

[45] Date of Patent: Jun. 10, 1997

[54] PROCESS FOR THE PREPARATION OF N-CARBONYLARYLIMINES USEFUL IN THE SYNTHESIS OF THERAPEUTICALLY ACTIVE TAXOIDS

[75] Inventors: Didier Bernard, Lyons; Patrick Leon, Tassin La Demi Lune, both of France

[73] Assignee: Rhone-Poulenc Rorer S.A., Antony, France

[21] Appl. No.: 578,652

[22] PCT Filed: Jul. 13, 1994

[86] PCT No.: PCT/FR94/00880

§ 371 Date: Jan. 16, 1996

§ 102(e) Date: Jan. 16, 1996

[87] PCT Pub. No.: WO95/02576

PCT Pub. Date: Jan. 26, 1995

[30] Foreign Application Priority Data

Jul. 16, 1993 [FR] France ..................... 93 08752

[51] Int. Cl.$^6$ ................................................ C07C 303/00
[52] U.S. Cl. ........................... 560/12; 560/24; 564/185
[58] Field of Search ..................... 560/12, 24; 564/185

[56] References Cited

PUBLICATIONS

Archiv Der Pharmazie; vol. 307, No. 8, pp. 653–655 1974.

*Primary Examiner*—Samuel Barts
*Attorney, Agent, or Firm*—Finnegan, Henderson, Farabow, Garrett & Dunner, L.L.P.

[57] ABSTRACT

A process for the preparation of N-carbonylarylimine of the general formula I:

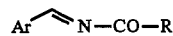

in which Ar represent an aryl radical and R represent a phenyl or t-butoxy radical, by desulphonating the compound of the general formula II.

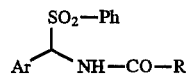

The compounds of formula II are novel when R is t-butoxy.

11 Claims, No Drawings

PROCESS FOR THE PREPARATION OF N-CARBONYLARYLIMINES USEFUL IN THE SYNTHESIS OF THERAPEUTICALLY ACTIVE TAXOIDS

This application is a 371 of PCT/FR94/00880 filed Jul. 13, 1994.

The present invention relates to a process for the preparation of N-carbonylarylimines of general formula:

$$Ar-N=CO-R \quad (I)$$

in which Ar represents an aryl radical and R represents a phenyl or t-butoxy radical.

In the general formula (I), Ar represents an aryl radical and R represents a phenyl or t-butoxy radical.

More particularly, Ar represents a phenyl or α- or β-naphthyl radical optionally substituted with one or more atoms or radicals chosen from halogen atoms, (fluorine, chlorine, bromine or iodine) and alkyl, alkenyl, alkynyl, aryl, arylalkyl, alkoxy, alkylthio, aryloxy, arylthio, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, dialkylcarbamoyl, cyano, nitro and trifluoromethyl radicals, it being understood that the alkyl radicals and the alkyl portions of the other radicals contain 1 to 4 carbon atoms, that the alkenyl and alkynyl radicals contain 2 to 8 carbon atoms and that the aryl radicals are phenyl or α- or β-naphthyl radicals, or alternatively Ar represents a 5-membered aromatic heterocyclic radical containing one or more atoms, which may be identical or different, chosen from nitrogen, oxygen or sulphur atoms, which are optionally substituted with one or more substituents, which may be identical or different, chosen from halogen atoms (fluorine, chlorine, bromine or iodine) and alkyl radicals containing 1 to 4 carbon atoms, aryl radicals containing 6 to 10 carbon atoms, alkoxy radicals containing 1 to 4 carbon atoms, aryloxy radicals containing 6 to 10 carbon atoms, amino radicals, alkylamino radicals containing 1 to 4 carbon atoms, dialkylamino radicals in which each alkyl part contains 1 to 4 carbon atoms, acylamino radicals in which the acyl part contains 1 to 4 carbon atoms, alkoxycarbonylamino radicals containing 1 to 4 carbon atoms, acyl radicals containing 1 to 4 carbon atoms, arylcarbonyl radicals in which the aryl part contains 6 to 10 carbon atoms, cyano, carboxyl and carbamoyl radicals, alkylcarbamoyl radicals in which the alkyl part contains 1 to 4 carbon atoms, dialkylcarbamoyl radicals in which each alkyl part contains 1 to 4 carbon atoms, and alkoxycarbonyl radicals in which the alkoxy part contains 1 to 4 carbon atoms.

More particularly, Ar represents a phenyl, 2- or 3-thienyl or 2- or 3-furyl radical optionally substituted with one or more atoms or radicals, which may be identical or different, chosen from halogen atoms and alkyl, alkoxy, amino, alkylamino, dialkylamino, acylamino, alkoxycarbonylamino and trifluoromethyl radicals.

Even more particularly, Ar represents a phenyl radical optionally substituted with a chlorine or fluorine atom or with an alkyl (methyl), alkoxy (methoxy), dialkylamino (dimethylamino), acylamino (acetylamino) or alkoxycarbonylamino (tert-butoxycarbonylamino) radical or 2- or 3-thienyl or 2- or 3-furyl radical.

According to the invention, the N-carbonylarylimines of general formula (I) may be prepared by the action of a base on a sulphone of general formula:

$$Ar-\overset{SO_2-Ph}{\underset{NH-CO-R}{C}} \quad (II)$$

in which Ar and R are defined as above and Ph represents a phenyl radical which is optionally substituted, for example with a methyl radical.

Generally, the process is performed in the presence of an alkali metal carbonate such as sodium carbonate or potassium carbonate, in an organic solvent chosen from ethers (tetrahydrofuran) and aromatic hydrocarbons (benzene or toluene), at a temperature between 50 and 100° C.

The sulphone of general formula (II) may be prepared, optionally in situ, by the action of an alkali metal phenylsulphinate such as sodium phenylsulphinate or potassium phenylsulphinate, on a mixture of an aldehyde of general formula:

$$Ar-CHO \quad (III)$$

in which Ar is defined as above, and a product of general formula $$H_2N-CO-R \quad (IV)$$

in which R is defined above, working in an aqueous-organic medium such as a mixture of water and an aliphatic alcohol containing 1 to 3 carbon atoms (methanol or ethanol), in the presence of an acid such as formic acid.

The N-carbonylarylimines of general formula (I) are particularly useful for stereoselectively preparing β-phenylisoserine derivatives of general formula:

$$\underset{Ar}{\overset{R-CO}{\underset{N}{\diagdown}}\!\!\diagup\!\!\overset{H}{\diagup}}\overset{O}{\underset{O-G_1}{\diagdown}}OH \quad (V)$$

in which Ar and R are defined as above and $G_1$ represents a protecting group for the hydroxyl function chosen from methoxymethyl, 1-ethoxyethyl, benzyloxymethyl, 2,2,2-trichloroethoxymethyl, tetrahydrofuranyl, tetrahydropyranyl and β-trimethylsilylethoxymethyl radicals, and trialkylsilyl radicals in which each alkyl part contains 1 to 4 carbon atoms, or a radical $-CH_2-Ph_1$ in which $Ph_1$ represents a phenyl radical optionally substituted with one or more atoms or radicals, which may be identical or different, chosen from halogen atoms and alkyl or alkoxy radicals containing 1 to 4 carbon atoms.

The β-phenylisoserine derivatives of general formula (V) are particularly useful for preparing the therapeutically active taxoids of general formula:

(VI)

in which Ar and R are defined as above and $R_1$ represents a hydrogen atom or an acetyl radical, in a process which consists in reacting a product of general formula (V) with a derivative of baccatin III or of 10-deacetylbaccatin III of general formula:

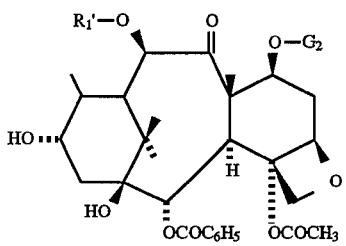 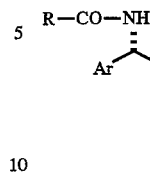 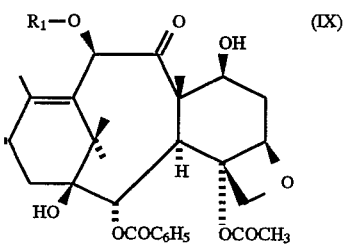

in which $R'_1$ represents an acetyl radical or a protecting group for the hydroxyl function such as a 2,2,2-trichloroethoxycarbonyl radical and $G_2$ represents a protecting group for the hydroxyl function such as a 2,2,2-trichloroethoxycarbonyl or trialkylsilyl radical, in order to obtain a product of general formula:

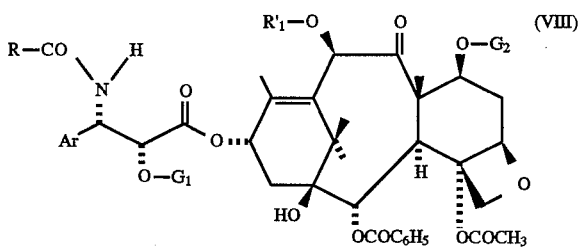

in which Ar, R, $R'_1$, $G_1$ and $G_2$ are defined as above, the protecting groups $G_1$, $G_2$ and optionally $R'_1$ of which are simultaneously or successively replaced by hydrogen atoms.

Generally, the esterification of a product of general formula (VII) by a product of general formula (V) is carried out in the presence of a coupling agent such as a carbodiimide, for instance dicyclohexylcarbodiimide, or a reactive carbonate, for instance 2-pyridyl carbonate, and an activating agent such as an aminopyridine, for instance 4-dimethylaminopyridine or 4-pyrrolidinopyridine, working in an organic solvent such as an aromatic hydrocarbon (benzene, toluene, xylene, ethylbenzene, isopropylbenzene, or chlorobenzene), an ether (tetrahydrofuran), a nitrile (acetonitrile) or an ester (ethyl acetate), at a temperature between 0° and 90° C.

When $G_1$ represents a methoxymethyl, 1-ethoxyethyl, benzyloxymethyl, 2,2,2-trichloroethoxymethyl, tetrahydrofuranyl, tetrahydropyranyl or β-trimethylsilylethoxymethyl radical or a trialkylsilyl radical in which the alkyl radicals contain 1 to 4 carbon atoms, replacement of the protecting groups $G_1$, $G_2$ and optionally $R'_1$ in the product of general formula (VIII) is carried out either using zinc, optionally in combination with copper, in the presence of an inorganic or organic acid such as hydrochloric acid or acetic acid, optionally in solution in an aliphatic alcohol containing 1 to 3 carbon atoms, when one of the protecting groups represents a 2,2,2-trichloroethoxycarbonyl radical, or by treatment using an inorganic or organic acid such as hydrochloric acid or acetic acid, optionally in solution in an aliphatic alcohol containing 1 to 3 carbon atoms, when one of the protecting groups represents a silyl radical.

When $G_1$ represents a radical —$CH_2$—$Ph_1$ or optionally a benzyloxymethyl radical, replacement of the protecting groups $G_2$ and optionally $R'_1$ by hydrogen atoms is first carried out under the conditions described above, in order to obtain the product of general formula:

in which R, Ar and $R_1$ are defined as above, the group $Ph_1$-$CH_2$— or optionally the benzyloxymethyl group which is replaced by a hydrogen atom, in order obtain the product of general formula (VI).

Replacement of the group $Ph_1$-$CH_2$— or optionally the benzyloxymethyl group of the product general formula (IX) by a hydrogen atom is generally carried out by hydrogenolysis using hydrogen in the presence of a catalyst such as palladium on charcoal, working in an organic solvent such as acetic acid, at a temperature between 0° and 60° C., preferably in the region of 40° C. It may be advantageous to work under pressure and optionally in the presence of a amount of an acid such as perchloric acid. The same replacement is also carried out by the action of dichlorodicyanobenzoquinone (DDQ) in an organic solvent such as dichloromethane or acetonitrile.

The taxane derivatives of general formula (VI) thus obtained may optionally be purified by application of the usual techniques.

The products of general formula (V) may be obtained by the action of an N-carbonylarylimine of general formula (I) on the anion of an optically active amide of a protected hydroxyacetic acid of general formula:

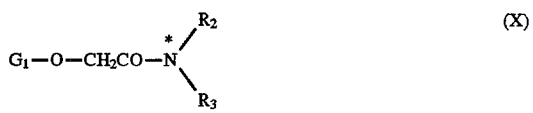

in which $G_1$ is defined as above and

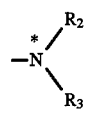

represents the residue of an optically active organic base, followed by hydrolysis of the product thus obtained of general formula:

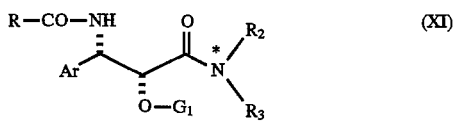

in which R, Ar, $G_1$ and

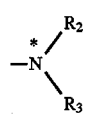

are defined as above.

It is particularly advantageous to use an amide of general formula (X) in which

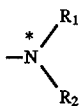

represents an L-(+)-2,10-camphorsultam residue of formula:

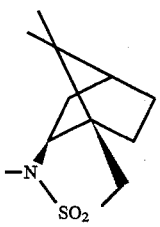

The process is generally carried out by reacting the N-carbonylarylimine of general formula (I), optionally prepared in situ, with the amide of the pre-anionized protected hydroxyacetic acid. The anionization is generally carried out using an alkali metal amide. Among the suitable amides which may be mentioned are the bis(trimethylsilyl)amide of sodium (NHMDS), of lithium (LHMDS) or of potassium (KHMDS), lithium diisopropylamide (LDA), lithium diethylamide (LDEA), lithium dicyclohexylamide (LDCHA), $(CH_3)_3SiN(R')Li$ (R'=alkyl, cycloalkyl or aryl) and tBuLi. Of most particular interest is lithium bis(trimethylsilyl)amide, which makes it possible to obtain a high yield and excellent stereoselectivity.

The anionization is generally carried out in an inert organic solvent such as an ether, for instance tetrahydrofuran, at a temperature below 0° C. and preferably in the region of −78° C.

The action of the product of general formula (I) on the pre-anionized product of general formula (X) is generally carried out in the same solvent and at the same temperature.

The product of general formula (XI) is hydrolysed to a product of general formula (V) using an inorganic base such as sodium hydroxide, potassium hydroxide or lithium hydroxide in aqueous or aqueous-organic medium. It is particularly advantageous to work in a tetrahydrofuran-water mixture in the presence of aqueous hydrogen peroxide solution. The reaction temperature is generally between −10° and 20° C. and preferably in the region of 0° C.

The examples which follow illustrate the present invention.

EXAMPLE 1

1200 cm³ of water, 600 cm³ of methanol, 70.2 g of t-butyl carbamate (0.6 mol) and 236.1 g of sodium phenylsulphinate (1.44 mol) are introduced into a 3-litre three-necked round-bottomed flask fitted with a mechanical paddle-stirrer, a thermometer and a dropping funnel, followed by addition of 127.2 g of benzaldehyde (1.2 mol). The mixture is stirred at a temperature in the region of 20° C. until the dissolution is complete, followed by addition, over 15 minutes, of 45.2 cm³ of pure formic acid (d =1.22) (1.2 mol). After 30 minutes the medium becomes cloudy. The stirring is continued for 18 hours and the precipitate formed is then separated out by filtration on a sinter funnel. The precipitate is washed with 200 cm³ of isopropyl ether and is then dried under reduced pressure. 144.5 g of N-t-butoxycarbonyl-α-phenylsulphonylbenzylamine, whose structure is confirmed by the proton nuclear magnetic resonance spectrum and the mass spectrum, are thus obtained in a yield of 69.4%.

The sulphone thus obtained (6.94 g; 0.02 mol) is dissolved in 60 cm³ of anhydrous toluene followed by addition of 3.31 g of potassium carbonate (0.024 mol). The mixture is heated, with stirring, at a temperature in the region of 80° C. for 3 hours. 20 cm³ of toluene are added. After cooling and filtration of the reaction mixture, the filtrate is concentrated to dryness under reduced pressure. 3.80 g of N-t-butoxycarbonylbenzylimine are thus obtained in the form of a colourless oil, in a yield of 93%, the characteristics of which product are as follows:

infrared spectrum (film): characteristic absorption bands at 3050, 2970, 2925, 1730, 1650, 1590, 1485, 1460, 1320, 1275, 1260, 1155, 1000, 980, 885, 850, 755 and 690 cm⁻¹.

proton NMR spectrum (360 MHz; CDCl₃): 1.52 (s, 9H); 7.39–7.49 (m, 3H); 7.84 (m, 2H); 8.80 (s, 1H).

EXAMPLE 2

10 g of the sulphone obtained above (28.8 mmol), 150 cm³ of anhydrous tetrahydrofuran and 18.3 g of pre-dried sodium carbonate (172.7 mmol) are introduced into a 500 cm³ reactor. The mixture is heated at reflux for 15 hours and 20 minutes. After cooling to a temperature in the region of 5° C. and filtration, the filtrate is concentrated to dryness. 5.66 g of pure N-t-butoxycarbonylbenzylimine, whose characteristics are identical to those of the product obtained in Example 1, are thus obtained in a yield of 96% after purification.

In the claims:

1. A process for the preparation of an N-carbonylarylimine of formula I:

in which Ar represents an aryl radical and R represents a phenyl or t-butoxy radical, wherein a sulphone of formula II:

in which Ar and R are defined as above and Ph represents an unsubstituted or substituted phenyl radical, is desulphonated.

2. The process according to claim 1, wherein the desulphonation is carried out in the presence of a base.

3. The process according to claim 2, wherein the base is selected from alkali metal carbonates.

4. The process according to claim 1, wherein it is performed in an organic solvent selected from ethers and aromatic hydrocarbons.

5. The process according to claim 1, wherein it is performed at a temperature in the range of 50° to 100° C.

6. The process according to claim 1 for the preparation of an N-carbonylarylimine of formula I:

in which, R is defined as in claim 1, and Ar represents a phenyl or α- or β-napthyl radical unsubstituted or substituted with one or more atoms or radicals selected from halogen atoms and alkyl, alkenyl, alkynyl, aryl, arylalkyl, alkoxy, alkylthio, aryloxy, arylthio, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, dialkylcarbamoyl, cyano, nitro and trifluoromethyl radicals, wherein the alkyl radicals and the alkyl portions of the other radicals contain 1 to 4 carbon atoms, the alkenyl and alkynyl radicals contain 2 to 8 carbon atoms and the aryl radicals are phenyl or α- or β-naphthyl radicals, or alternatively Ar represents a 5-membered aromatic heterocyclic radical containing one or more atoms, which may be identical or different, selected from nitrogen, oxygen or sulphur atoms, which are unsubstituted or substituted with one or more substituents, which may be identical or different, selected from halogen atoms and alkyl radicals containing 1 to 4 carbon atoms, aryl radicals containing 6 to 10 carbon atoms, alkoxy radicals containing 1 to 4 carbon atoms, aryloxy radicals containing 6 to 10 carbon atoms, amino radicals, alkylamino radicals containing 1 to 4 carbon atoms, dialkylamino radicals in which each alkyl part contains 1 to 4 carbon atoms, acylamino radicals in which the acyl part contains 1 to 4 carbon atoms, alkoxycarbonylamino radicals containing 1 to 4 carbon atoms, acyl radicals containing 1 to 4 carbon atoms, arylcarbonyl radicals in which the aryl part contains 6 to 10 carbon atoms, cyano, carboxyl and carbamoyl radicals, alkylcarbamoyl radicals in which the alkyl part contains 1 to 4 carbon atoms, dialkylcarbamoyl radicals in which each alkyl part contains 1 to 4 carbon atoms, and alkoxycarbonyl radicals in which the alkoxy part contains 1 to 4 carbon atoms.

7. The process according to claim 6 wherein the halogen atom is selected from the group consisting of fluorine, chlorine, bromine, and iodine atoms.

8. A sulphone of formula II:

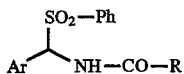

(II)

in which Ar is an aryl radical, R represents a t-butoxy radical and Ph represents an unsubstituted or substituted phenyl radical.

9. The sulphones according to claim 8 wherein Ar represents a phenyl or α- or β-napthyl radical unsubstituted or substituted with one or more atoms or radicals selected from halogen atoms and alkyl, alkenyl, alkynyl, aryl, arylalkyl, alkoxy, alkylthio, aryloxy, arylthio, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, dialkylcarbamoyl, cyano, nitro and trifluoromethyl radicals, wherein the alkyl radicals and the alkyl portions of the other radicals contain 1 to 4 carbon atoms, the alkenyl and alkynyl radicals contain 2 to 8 carbon atoms, and the aryl radicals are phenyl or α- or β-naphthyl radicals, or alternatively Ar represents a 5-membered aromatic heterocyclic radical containing one or more atoms, which may be identical or different, selected from nitrogen, oxygen or sulphur atoms, which are unsubstituted or substituted with one or more substituents, and alkyl radicals containing 1 to 4 carbon atoms, aryl radicals containing 6 to 10 carbon atoms, alkoxy radicals containing 1 to 4 carbon atoms, aryloxy radicals containing 6 to 10 carbon atoms, amino radicals, alkylamino radicals containing 1 to 4 carbon atoms, dialkylamino radicals in which each alkyl part contains 1 to 4 carbon atoms, acylamino radicals in which the acyl part contains 1 to 4 carbon atoms, alkoxycarbonylamino radicals containing 1 to 4 carbon atoms, acyl radicals containing 1 to 4 carbon atoms, arylcarbonyl radicals in which the aryl part contains 6 to 10 carbon atoms, cyano, carboxyl and carbamoyl radicals, alkylcarbamoyl radicals in which the alkyl part contains 1 to 4 carbon atoms, dialkylcarbamoyl radicals in which each alkyl part contains 1 to 4 carbon atoms, and alkoxycarbonyl radicals in which the alkoxy part contains 1 to 4 carbon atoms.

10. The sulphones according to claim 9 wherein the halogen atom is selected from the group consisting of fluorine, chlorine, bromine, and iodine atoms.

11. A process for preparing sulphones of formula (II):

(II)

wherein Ar represents an aryl radical, R represents a t-butoxy radical, and Ph represents an unsubstituted or substituted phenyl radical;

by reacting an alkali metal phenylsulphinate with a mixture of an aldehyde of formula III:

Ar—CHO (III)

wherein Ar is defined as above; and a product of formula IV:

H$_2$N—CO—R (IV)

wherein R is defined above;

in an aqueous-organic medium in the presence of an acid.

* * * * *